United States Patent [19]

Speaker et al.

[11] Patent Number: 4,743,583

[45] Date of Patent: May 10, 1988

[54] SUSTAINED RELEASE PROTEIN COMPOSITIONS AND METHOD FOR MAKING

[75] Inventors: Tully J. Speaker; Tycho J. Speaker, both of Philadelphia, Pa.

[73] Assignee: Temple University, Philadelphia, Pa.

[21] Appl. No.: 75,092

[22] Filed: Jul. 20, 1987

[51] Int. Cl.[4] .......................... C07K 1/02; C07K 1/14; C07K 3/24; C07K 3/28
[52] U.S. Cl. ............................................ 514/4; 514/8; 514/21; 530/304; 530/399; 530/419; 530/420; 530/423; 530/425; 530/427
[58] Field of Search ............... 530/419, 420, 425, 423, 530/427, 304, 399; 514/4, 8, 21

[56] References Cited

U.S. PATENT DOCUMENTS

| | | | |
|---|---|---|---|
| 3,875,138 | 4/1975 | Jackson | 530/304 X |
| 3,959,457 | 5/1976 | Speaker et al. | 514/297 X |
| 4,489,133 | 12/1984 | Kornberg | 530/423 X |
| 4,659,568 | 4/1987 | Heilman, Jr. | 530/423 X |
| 4,668,584 | 5/1987 | Uzgiris et al. | 530/427 X |

Primary Examiner—Howard E. Schain
Attorney, Agent, or Firm—Ratner & Prestia

[57] ABSTRACT

Lewis acid-Lewis base high molecular weight salt microparticulate material of the type referred to in U.S. Pat. No. 3,959,457, which include biologically active peptides and proteins solubilized in a non-aqueous, non-denaturing manufacturing solvent.

18 Claims, No Drawings

SUSTAINED RELEASE PROTEIN COMPOSITIONS AND METHOD FOR MAKING

BACKGROUND OF THE INVENTION

This invention pertains to a novel sustained release delivery form for biologically active peptides and proteins, and to a method for making such material.

Microencapsulation is a technique of enclosing core materials in a polymeric membrane to produce microparticles.

In the pharmaceutical industry, considerable interest has been generated by the use of microparticles as sustained release delivery formulations for naturally occurring and synthetic drugs. Of particular interest is the use of microparticles as delivery mechanisms for regulatory hormones, such as biologically active peptides and proteins. However, many of the methods for making are of limited utility because of the inability of the manufacturing method to encapsulate a subject compound without destroying the biological activity of the encapsulated material.

Other problems with known prior art microparticulate material arise from the fact that generally such material tends to be of unsuitable size for intravenous injection. Such material also tends to agglomerate, thus deleteriously effecting certain important properties of the materials such as dispersibility. Additionally, microparticulate material which is of suitable size for injection may also be captured by the reticulo-endothelial system, which may have deleterious effects on blood clearance of the microparticle shell material and tissue distribution of the encapsulated core material.

Furthermore, some microparticulate formulations which are suitable for encapsulation of bioactive proteins or peptide molecules (e.g. liposome particles) are limited in their capacity to encapsulate core material because they utilize as a core an aqueous solution in which the bioactive material has necesssarily only limited solubility.

A specific type of microparticulate material and a method of making such material is disclosed in U.S. Pat. No. 3,959,457 (of common inventorship and assignment herewith). This material is comprised of the reaction product produced at the inter phase boundary of a finely dispersed emulsion, comprising;

(I) a water immiscible solution of an organic polyfunctional Lewis base in a low boiling point, slightly polar, organic solvent; and (II) an aqueous solution of a partially hydrophilic, partially lipophilic, polyfunctional Lewis acid.

Microparticles of this type comprise a multiplicity of closed structures formed of lattice-like high molecular weight salt molecules of the Lewis acid and Lewis base, through which the encapsulated core material diffuses. The rate of diffusion is controlled by both the particle or molecular size of the encapsulated compound and by the openness of the lattice or network of molecules comprising the particle walls. The degree of openness of the lattice is controlled by the spacing of reactive sites on the high molecular weight polyfunctional Lewis acids and by the thickness of the particle walls.

In Lewis acid-Lewis base salt microparticles, of the type referred to above, the degree to which peptides and proteins may be encapsulated is limited. Many biologically active peptides and proteins are either insoluble or unstable in polar organic manufacturing solvents of the type typically used in making these microparticles. These solvents tend to denature or otherwise damage the subject peptide or protein, thus diminishing biological activity.

BRIEF DESCRIPTION OF THE INVENTION

This invention comprises novel polypeptide delivery forms consisting essentially of a biologically active peptide or protein (sometimes referred to herein as a "polypeptide,") incorporated in a Lewis acid - Lewis base high molecular weight salt microparticulate material of the type referred to above, in which the organic manufacturing solvent is a solvent for the Lewis base wall-forming component and is also a non-denaturing solvent which is capable of effectively solubilizing a proteinaceous macromolecule core material. The polypeptides useful herein are biologically active peptides and proteins, having from nominally 14 to 1000 amino acids. Such peptides and proteins may consist of single or multiple amino acid polymer chains and must be able to diffuse out of the individual microparticulate material. The non-denaturing solvents useful herein include non cyclic esters, cyclic esters or lactones, cyclic amides and linear amides, having Hildebrand solubility parameters or Hildebrand delta values of from about 20 to about 30. Such solvents are preferably ethyl acetate, butyrolactone valerolactone and caprolactone, N-methyl-gamma pyrrolidinone and N-methylformamide, respectively.

In some instances, these organic solvents may be used in place of or in combination with the slightly polar organic solvents of U.S. Pat. No. 3,959,437.

DETAILED DESCRIPTION OF THE INVENTION

Generally, microparticles of the type to which this invention is directed are made as follows:

A non-aqueous solution of a Lewis base in a slightly polar organic solvent is added to an aqueous solution of a Lewis acid, such as a acacia gum, arabic acid or carboxymethylcellulose. The Lewis base is preferably, a polyfunctional Lewis base, such as piperazine or triethylenediamine or ethylene diamine. However, monofunctional Lewis bases, such as triethylamine may also be used.

These solutions are combined with rapid dispersion or mixing to produce a finely dispersed emulsion of organic phase droplets in a continuous aqueous phase.

Included in the non-aqueous solvent in accordance with the present invention, is a "polypeptide" core material. As used herein, "polypeptide" refers to biologically active polymeric compounds made up of from nominally 14 to 1000 amino acids which may consist of single or multiple amino acid polymer chains. These peptides and proteins are preferably soluble in the organic solvents of the present invention, although it is also possible to encapsulate partially solubilized proteins or protein suspensions using the methods and materials disclosed herein. However, use of a protein solution for encapsulation is preferable, as it allows much more careful control of the resultant particle size and ultimately the dispersability of the encapsulated compounds.

Typically, polypeptide preparations are made from a lyophilized or "freeze dried" form of a biologically derived peptide or protein. Biologically derived means that the sources of these peptides or proteins are usually tissue or organ preparations from which biologically active constituent material is extracted. However, it is recognized that these sources of polypeptides are not limitations and that "polypeptides" as used herein is meant to include other non-conventionally derived peptides and proteins, such as may be produced by peptide synthesis or by genetically altered microorganisms.

With respect to the three dimensional or conformational structure of these polypeptides, the protein/peptide compounds may be relatively linear or complex three dimensional structures. Representative of such compounds are growth hormone (somatotrophin), insulin and glucagon. Growth hormones of various species, for example, differ in exact amino sequence but typically have molecular weights near 30,000 atomic mass units. Insulins of various species also differ in amino acid sequence but have molecular weights in the range near 7000 atomic mass units. For purpose of release of the polypeptide core material, it must be of such molecular size and conformation that it is capable of diffusional escape from the individual microparticular material. However, it should not be inferred that the active core material must escape rapidly. Indeed, sustained release of such bioactive material, such as growth hormone or insulin, over periods of days or weeks may be preferred. Many bioactive peptides are highly potent materials of which only small amounts are required to produce substantial effects. Thus, for example, release of only a fraction of a milligram of growth hormone per day is adequate for therapeutic purposes.

In the organic phase droplets of the finely dispersed emulsion of the aqueous and non-aqueous solutions, the Lewis base is drawn to the surface of the droplet by the polar attraction of the surrounding aqueous phase. In the aqueous phase, the partially hydrophilic, partially lipophilic, polyfunctional Lewis acid is drawn, due to its partially lipophilic characteristic towards the interface between the organic droplet and the surrounding aqueous phase. The acid reacts, presumably through dipole and/or ionic bonding, with the Lewis base concentrated on the outer surfaces of the organic phase droplets adjacent the interface, to produce a shell-like insoluble particle containing the core material. The resultant microparticle generally corresponds in shape and size to the dispersed organic droplets in the reactant emulsion. Each of these shell-like particles is thought to consist of an open network, or lattice of molecules of a dipole and/or ionic salt.

The reaction of the polyfunctional Lewis acid and the Lewis base is thought to be essentially a two step reaction sequence resulting in the formation of anisotropic salt films in small spherical or sphere like shapes sometimes referred to as microcapsules. The generalized reaction sequence is more clearly set forth in U.S. Pat. No. 3,959,457.

Although it is widely recognized that most proteins are generally not soluble or stable in non-aqueous solvents of the type typically used in the manufacture of microparticles of the type referred to above, organic solvents of the instant invention are capable of approximating and in some instances exceeding the ability of aqueous systems to dissolve proteins. Furthermore, these organic solvents are capable of effectively solubilizing peptides and proteins without denaturing the peptide or protein, thus preserving its biological activity. Additionally, these solvents are also suitable solvents for the Lewis base wall-forming component of the Lewis acid-Lewis base microparticle. Typical preferred solvents which may serve in such a manner include, but are not limited to, non-cyclic esters such as ethyl acetate; cyclic esters or lactones such as butyrolactone, valerolactone and caprolactone; linear amides such as N-methylformamide, N-methylacetamide, N,N-diemthylformamide, N,N-diemthylacetamide, N-ethylacetamides; and cyclic amides such as N-methylgamma pyrrolidinone.

It is of particular note that some of the organic solvents which are useful as protein solvents and for the manufacture of the microparticles of the present invention are quite water soluble/water miscible. Therefore, they differ in a fundamental characteristic from the water-immiscible organic solvents described in U.S. Pat. No. 3,959,457. Such solvents are ordinarily not useful in the production of microcapsules. However, these water soluble/water miscible solvents may be advantageously employed as solvents in the manufacture of new microparticles containing proteins and peptides by either:

a. mixing a protein solution (e.g. growth hormone in butyrolactone) with an approximately equal volume of a water-immisible solvent (such as dichloromethane) containing the Lewis base and emulsifying the organic solvent mixture in the wall forming step; or b. taking advantage of the tendency of concentrated solutions of protein or peptide in certain organic solvents (e.g. growth hormone in N-methylformamide) to increase viscosity to the point of gelation and, gelled, to be much less rapidly water-miscible.

In the latter instance, a solution of Lewis base in organic solvent is used to prepare a concentrated highly viscid solution of the peptide. This viscid, slowly water-miscible solution is then utilized in the wall forming step as if it were truely water immiscible.

Typical of such useful protein solvents, which are also water-soluble/water-miscible, are butyrolactone, N-methylformamide and N-methylacetamide. Such solvents also rapidly diffuse from the capsules once the walls have been formed. This rapid diffusion and the water solubility of these solvents also facilitate separation and removal of the organic manufacturing solvent by, for example, dialysis or centrifugation.

Whether a given solvent is suitable for solubilizing proteins depends, inter alia, on the structure of the protein/peptide and the exposed solvent-interactive surface of the protein/peptide. The mechanisms by which solute molecules interact with solvent molecules to form solutions is thought to involve a process in which energy is expended. The energy expended and transferred in such a process is derived from the breaking of old and the making of new associative van der Walls, dipole, hydrogen and ionic bonds and from the initial thermal energy of the system. If approximately equal amounts of energy are expended in weakening the old self-associations of solute and solvent molecules respectively in forming new solute-solvent associative bonds, a solute is relatively more soluble in a solvent then it is if there is a great disparity in the amounts of energy required in the various steps of the solvation/solution process. Simply stated, a solute having an energy value near that of the solvent will be more readily dissolved by that solvent than by a solvent having a much different energy value. The Hildebrand theory of solution and its intellectual descendants describe the process with mathematical rigor. Often suitable solvents for such applications may be selected from those having Hildebrand solubility parameter values (sometimes referred to as cohesive energy density or Hildebrand delta values) in the range from about 20 to about 30 MPa$^{\frac{1}{2}}$ (i.e. the square root of the mega-Pascal value), as described in A.F.M. Barton's *Handbook of Solubility Parameters and Other Cohesion Parameters*, CRC Press, Boca Raton, Fla. 1983.

An exact solubility parameter range cannot be rigorously defined since examination of Barton shows that for any single substance several (usually) slightly different values of this parameter have been measured or calculated by different workers. As a guide, it may be useful to note the Hildebrand values reported for some solvents mentioned above:

| Solvent | MPa$^{\frac{1}{2}}$ |
| --- | --- |
| Dichloromethane | 19.8 |
| N,N—diethylacetamide | 20.2 |
| N,N—diethylformamide | 21.7 |
| butyrolactone | 26.3 |
| N—ethylformamide | 28.4 |
| N—methylformamide | 32.9 |
| water | 47.9 |

Many proteins and peptides are large complex molecules capable of folding and coiling about themselves in such a manner as to expose only some parts of the molecule while masking other parts. In some instances, interaction with a solvent alters the degree or type of folding and coiling of a protein. Thus, while Hildebrand values are illustrative of the solvating capacity of a given solvent, it is the exposed solvent-interactive surface of the protein or peptide which may be a primary determinant of which organic solvent will be the most effective in dissolving the polypeptide.

Alternatively, the solute-solvent interaction may be considered in the dissolution of the polypeptide. The partial cohesive energy parameters of Hansen (which take into account other interactions such as dipole, van der Waals and hydrogen bonding contributions to cohesive energy) may may also be used in selecting organic solvents with which to dissolve proteins and peptides. One preferably selects as candidate solvents those which have Hildebrand (Hansen) parameters near that of the material to be dissolved. Since these parameters are not readily (if at all) available for most proteins or peptides, they may be estimated from constituent values described by R. F. Fedors, Polym. Eng. Sci., Vol. 14, pgs. 147 and 472 (1974).

Alternatively, one may proceed by measuring the solubility of a protein in a series of organic solvents with graded Hildebrand delta value. Solute solubility will increase as solute and solvent approach one another in delta value.

GENERAL PROCEDURES FOR FORMING MICROCAPSULES

In all instances where an aqueous solution is utilized as the continuous phase for the dispersion or emulsification of a second solution of materials dissolved in an organic solvent, it is preferred, but not essential, that the organic solvent be slowly and steadily added to the aqueous solution over a period of approximately 30 seconds. In all instances, solutions are prepared and reactions take place at room temperature, unless otherwise stated. Any of several means to disperse or emulsify the organic solution in the aqueous medium may be employed including:

a. vigorously stirring the solution with a magnetically driven stirring bar at a nominal sheer rate of 700 or more cm/s;

b. vigorously mixing the solution with a multi-orifice axial turbine (such as a Brinkmann homogenizer PT10/35 and generator PST/10, Brinkmann Instruments, Westbury, N.Y.) at a nominal setting of 5; or c. vigorously agitating the solutions with an ultrasonic probe (such as Heat Systems model W185D, Ultrasonics, Inc., Plainview, N.Y.) at a nominal output of 100 watts.

By increasing or decreasing length of time and/or vigor of emulsification, droplet size (and resulting microparticle size) may be controlled.

EXAMPLE I FOR METHOD OF MAKING MICROCAPSULE PRODUCTS CONTAINING POLYPEPTIDE MATERIALS

An aqueous solution of arabic acid was prepared by adding to one gram of arabic acid, enough water to make 10 mL. Typically, the arabic acid is first wetted with a small amount of alcohol to assist in solubilizing the otherwise slowly solubilized Lewis acid. A non-aqueous solution was also prepared by adding anhydrous piperazine (in an amount stoichiometrically equivalent to the arabic acid), 0.005 g of somatotrophic hormone or somatotrophin (growth hormone), in enough butyrolactone to make 10 mL of solution.

The aqueous and non-aqueous solutions were then combined in a container and continuously agitated for approximately one minute, to produce an emulsion of organic droplets, approximately 5 microns in diameter, dispersed in and surrounded by continuous phase aqueous solution.

After agitation, the mixture was centrifuged (10,000 gravity minutes) and the supernatant fluid was removed from the viscid volume of packed newly formed microcapsules. The microcapsules were washed of manufacturing fluids and unreacted or excess reaction components by repeatedly suspending them in an equal volume of water. The suspended microparticles were separated by centrifuging (10,000 gravity minutes) and removing the supernatant. The resultant product was a flowable concentrate of microparticulate material comprising microcapsules consisting of shell-like films surrounding the protein core material.

EXAMPLE II FOR METHOD OF MAKING MICROCAPSULE PRODUCTS CONTAINING POLYPEPTIDE MATERIALS

An aqueous solution of arabic acid was prepared by adding to one gram of arabic acid, enough water to make 10 mL. A first non-aqueous solution was prepared by adding anhydrous piperazine (in an amount stochiometrically equivalent to the arabic acid) in enough dichloromethane to equal 2 mL. A second non aqueous solution was also prepared by adding 0.010 gram of somatotrophic hormone or somatotrophin (growth hormone) to enough N-methylformamide to make 8 mL.

The first and second non aqueous solutions were then combined and dispersed into the aqueous solution. The aqueous and non-aqueous mixture was then continuously agitated for approximately one minute, to produce an emulsion of organic droplets, approximately 5 microns in diameter, dispersed in and surrounded by continuous phase aqueous solution.

After agitation, the mixture was allowed to stand undisturbed for about 10 minutes and the supernatant suspension was removed from the small volume of dichloromethane which separated. Residual dichloromethane was removed by evaporation. The mixture was centrifuged (10,000 gravity minutes) and the supernatant fluid was removed from the highly viscid volume of packed newly formed microcapsules. The microcapsules were washed of manufacturing fluids and unreacted or excess reaction components, by repeatedly suspending them in an equal volume of water separating the suspended microparticles by centrifuging (10,000 gravity minutes), and removing the supernatant. The resulting product was a flowable concentrate of microparticulate material comprising microcapsules consisting of shell-like films surrounding the protein core material.

EXAMPLE III FOR METHOD OF MAKING MICROCAPSULE PRODUCTS CONTAINING POLYPEPTIDE MATERIALS

A solution of arabic acid was prepared by adding to one gram of arabic acid enough water to make 10 mL. A first non-aqueous solution was prepared by adding to anhydrous piperazine (in an amount stoichiometrically equivalent to the arabic acid) enough dichloromethane to make 2 mL. A second nonaqueous solution was also prepared by adding 0.01 gram of insulin to enough N-methylformamide to make 8 mL.

The first and second non-aqueous solutions were then combined and then dispersed into the aqueous solution with continuous and vigorous agitation for approximately one minute to produce an emulsion of organic droplets approximately 5 microns in diameter, dispersed in and surrounded by a continuous aqueous phase solution. After agitation, the mixture was allowed to stand undisturbed for about 10 minutes and the supernatant suspension was removed from the small volume of dichloromethane which separated. Residual dichloromethane was removed by evaporation. The mixture was centrifuged (10,000 gravity minutes) and the supernatant fluid was removed from the highly viscid volume of packed newly formed microcapsules. The microcapsules were washed of manufacturing fluids and unreacted or excess reaction components by repeatedly suspending them in an equal volume of water, separating the suspended microparticles by centrifuging (10,000 gravity minutes), and removing the supernatant. The resulting product was a flowable concentrate of microparticulate suspension comprising microcapsules consisting of shell-like films surrounding protein core material.

While this invention has been described with reference to specific, and particularly, preferred embodiments thereof, it is not limited thereto and the appended claims are intended to be construed to encompass not only the specific forms and variants of the invention shown but to such other forms and variants as may be devised by those skilled in the art without departing from the true spirit and scope of this invention.

We claim:

1. Microparticulate material, consisting essentially of the reaction product of an emulsion of:
   (a) a partially hydrophilic, partially lipophilic, polyfunctional Lewis acid in an aqueous solution, said solution comprising a continuous phase; and
   (b) a Lewis base dissolved in a non-aqueous solvent complex, said non-aqueous solvent complex comprising:
      (1) a water immiscible, non-denaturing solvent; or
      (2) a water miscible, protein non-denaturing solvent, rendered viscid and temporarily water immiscible by the inclusion therein of a high concentration of a protein solute; or
      (3) a combination of water immiscible solvent and a water-miscible protein non-denaturing solvent, said non-aqueous solvent complex comprising a discontinuous droplet phase, said continuous aqueous phase surrounding the droplets of said discontinuous phase,
   wherein, said Lewis acid and said Lewis base and said non-aqueous solvent are adapted by reaction of said Lewis acid and said Lewis base at the phase interface of the surfaces of said droplets to form enclosed cellular structures comprising a microparticulate material containing said core material in said closed structures, in a manner to permit controlled release of the core material through the microparticle wall,
   wherein said core material is a polypeptide having nominally from 14 to 1000 amino acids and is soluble in said non-aqueous, protein non-denaturing solvent and wherein said core material is diffusable through said microparticulate wall.

2. Microparticulate material as recited in claim 1 wherein said polypeptide is selected from the group consisting of insulin, glucagon and growth hormone.

3. Microparticulate material as recited in claim 2 wherein said polypeptide is insulin.

4. Microparticulate material as recited in claim 2 wherein said polypeptide is glucagon.

5. Microparticulate material as recited in claim 2 wherein said polypeptide is growth hormone.

6. Microparticulate material as set forth in claim 1 wherein said water-miscible, protein non-denaturing solvent is a cyclic ester having a Hildebrand solubility parameter of approximately 23 to approximately 32 MPa$^{\frac{1}{2}}$.

7. Microparticulate material as set forth in claim 6 wherein sai cyclic ester is butyrolactone.

8. Microparticulate material as set forth in claim 6 wherein said cyclic ester is valerolactone.

9. Microparticulate material as set forth in claim 6 wherein said cyclic ester is caprolactone.

10. Microparticulate material as set forth in claim 1 wherein said water miscible, protein nondenaturing solvent is a cyclic amide having a Hidlebrand solubility parameter of approximately 23 to 32 MPa$^{\frac{1}{2}}$.

11. Microparticulate material as recited in claim 10 wherein said cyclic amide is N-methyl-gammapyrrolidinone.

12. Microparticulate material as set forth in claim 1 wherein said water miscible, protein non-denaturing solvent is a linear amide having a Hildebrand solubility parameter of approximately 23 to 32 MPa$^{\frac{1}{2}}$.

13. Microparticulate material as set forth in claim 12 wherein said linear amide is selected from the group consisting of N-methylformamide, N-methylacetamine, N,N-dimethylformamide, N,N-dimethylacetamide and N-ethylacetamide.

14. Microparticulate material as set forth in claim 1 wherein said solvent comprises a first non-denaturing, solubilizing solvent for said polypeptide and a second solvent selected from the group consisting of chloroform, dichloromethane, dichloroethane, and methylethylketone.

15. Microparticulate material as recited in claim 14 wherein said solvent comprises a mixture of N-methylformamide and dichloromethane.

16. Microparticulate material as set forth in claim 15 wherein said polypeptide is growth hormone.

17. A method of producing mircroparticulate material containing biologically active peptides and proteins comprising:

(a) making a mixture of an aqueous solution of a partially hydrophilic, partially lipophilic, polyfunctional Lewis acid, with a non-aqueous solution of a polyfunctional Lewis base in an organic solvent, said solvent selected from the group consisting of non-cyclic esters, cyclic esters, cyclic amides and linear amides, said solvent further having a Hildebrand solubility parameter of approximately 23 to 32 $MPa^{\frac{1}{2}}$, said solvent further containing a core material consisting of a polypeptide having nominally between 14 and 1000 amino acids, (b) agitating said mixture to form an emulsion of water immiscible solution droplets surrounded by a continuous phase of said aqueous solution, wherein said Lewis acid and said Lewis base area adapted to react with one another at the common phase interface of said droplet surfaces to form microparticulate material comprising a multiplicity of closed cellular structures containing said core material;

(c) separating and washing and removing residual solvent from said microparticulate material.

18. A method as recited in claim 17 wherein said polypeptide is selected from the group consisting of glucagon, insulin and growth hormone.

* * * * *